United States Patent [19]

Minami et al.

[11] Patent Number: 5,221,342

[45] Date of Patent: Jun. 22, 1993

[54] COLORING COMPOSITION AND PRODUCTION METHOD AND USE THEREOF

[75] Inventors: Takashi Minami; Masayuki Naganuma; Yoshiaki Yagita; Takeshi Kawaura; Eiko Kinoshita, all of Yokohama, Japan

[73] Assignee: Shiseido Company Ltd., Tokyo, Japan

[21] Appl. No.: 766,892

[22] Filed: Sep. 25, 1991

Related U.S. Application Data

[63] Continuation of Ser. No. 519,356, May 3, 1990, abandoned, which is a continuation of Ser. No. 119,016, Nov. 10, 1987, abandoned.

[30] Foreign Application Priority Data

Nov. 10, 1986 [JP] Japan ................. 61-266868
Nov. 10, 1986 [JP] Japan ................. 61-266869

[51] Int. Cl.$^5$ .................... C09C 1/00; C04B 11/00
[52] U.S. Cl. ........................... 106/461; 106/772; 106/778; 424/63; 424/69
[58] Field of Search ............. 106/461, 772, 778; 424/63, 69

[56] References Cited

U.S. PATENT DOCUMENTS 2,177,251  10/1939  Hanahan ................. 106/461
4,724,138  2/1988  Duffy et al. ............. 424/63

OTHER PUBLICATIONS

Derwent Abstracts, AN 78-27729A/15, "Porous, Granular Agricultural and Gardening Soil", Japanese Patent, J53022045, Mar. 1, 1978.
Derwent Abstracts, AN 84-168725/27, "Rod-Shaped Cosmetic Material", Japanese Patent J59093014, May 29, 1984.

Primary Examiner—Mark L. Bell
Assistant Examiner—Anthony J. Green
Attorney, Agent, or Firm—Sprung Horn Kramer & Woods

[57] ABSTRACT

A coloring composition comprising (i) gypsum dihydrate and (ii) at least one coloring agent selected from the group consisting of inorganic pigments, organic pigments, dyestuffs, and natural coloring matters. This coloring composition may be produced by mixing (i) gypsum having, as water of crystallization, 0 to 0.5 mole, based on one mole of the gypsum, of water, (ii) at least one coloring agent selected from the group consisting inorganic pigments, organic pigments, dyestuffs, and natural coloring matters, and (iii) water or an aqueous solvent solution, and after solidification, powdering the resultant solid mixture.

The coloring composition can provide a clear color tone when formulated in, for example, cosmetics, and when completely dispersed in, for example, a cosmetic base material.

6 Claims, No Drawings

COLORING COMPOSITION AND PRODUCTION METHOD AND USE THEREOF

This application is a continuation of application Ser. No. 519,356, filed May 3, 1990, abandoned which is a continuation of Ser. No. 119,016, filed Nov. 10, 1987, now abandoned.

BACKGROUND OF THE INVENTION

1. Field of the Invention

The present invention relates to a coloring composition containing gypsum uniformly dispersed therein and capable of providing a clear color tone, and a production method thereof. The present invention also relates to a cosmetic composition containing the above-mentioned coloring composition formulated therein.

2. Description of the Related Art

Various coloring pigments including inorganic pigments such as iron red oxide, iron black oxide, and ultramarine blue and organic pigments such as red #201 (i.e., C.I. 15850 or Lithol Rubine B) and red #202 (i.e., C.I. 15850:1 or Lithol Rubine BCA) are formulated in various kinds of compositions including cosmetic compositions, coating compositions, and synthetic resin compositions, depending upon the use and purposes thereof. These coloring agents are either directly formulated, or formulated after mixing or blending, with extender pigments (or loading pigments) such as talc and mica, to ensure that the pigments are uniformly dispersed in the compositions.

However, when the extender pigments are used, the clarity of the coloring pigments in the formulated compositions is sometimes adversely affected and a complete dispersion of the coloring pigments is sometimes not effected in the composition, and thus not-well-dispersed pigments can be observed in the resultant compositions. Furthermore the color tone of the composition containing coloring pigments therein and the color tone upon application are sometimes different.

SUMMARY OF THE INVENTION

Accordingly, the objects of the present invention are to eliminate the above-mentioned disadvantages of the prior art and to provide a coloring composition having a good dispersibility in compositions to be formulated and capable of providing a clear color tone in the compositions to be formulated.

Another object of the present invention is to provide a method for producing the above-mentioned coloring composition.

A further object of the present invention is to provide a cosmetic composition containing the above-mentioned coloring composition formulated therein which is capable of providing a good color tone and a good finish, when applied, and which has a good applicability to the skin.

Other objects and advantages of the present invention will be apparent from the following description.

In accordance with the present invention, there is provided a coloring composition comprising (i) gypsum dihydrate and (ii) at least one coloring agent selected from the group consisting of inorganic pigments, organic pigments, dyestuffs, and natural coloring matters.

In accordance with the present invention, there is also provided a method for producing a coloring composition comprising the steps of:

mixing (i) gypsum having, as water of crystallization, 0 to 0.5 mole, based on one mole of the gypsum, of water, (ii) at least one coloring agent selected from the group consisting of inorganic pigments, organic pigments, dyestuffs, and natural coloring matters, and (iii) water or an aqueous solvent solution; and after solidification of the mixture, powdering the resultant solid mixture.

In accordance with the present invention, there is further provided a cosmetic composition containing (A) a cosmetic base and (B) a coloring composition comprising (i) gypsum dihydrate and (ii) at least one coloring agent selected from the group consisting of inorganic pigments, organic pigments, dyestuffs, and natural coloring matters.

DESCRIPTION OF THE PREFERRED EMBODIMENTS

According to the present invention, the desired coloring composition can be obtained by using gypsum. The gypsum usable in the present invention has 0 to 0.5 mole water of crystallization.

The inorganic pigments usable in the present invention include, for example, titanium dioxide, iron red oxide, iron yellow oxide, iron black oxide, carbon black, mango violet, cobalt violet, chromium oxide, chromium hydroxide, cobalt titanate, ultramarine blue, and Prussian blue.

The organic pigments usable in the present invention include, for example, Red #201 (C.I. 15850 or Lithol Rubine B), Red #202 (C.I. 15850:1 or Lithol Rubine BCA), Red #204 (C.I. 15585:1 or Lake Red CBA), Red #226 (C.I. 73360 or Helindone Pink CN), Yellow #401 (C.I. 11680 or Hansa Yellow), Blue #404 (C.I. 74160 or Phthalocyanine Blue).

The dyestuffs and natural coloring matters usable in the present invention may be any conventional dyestuffs and natural coloring matters which are harmless to the human body.

Typical examples of such dyestuffs are D & C Red No. 19 (C.I 45170), D & C Red No. 17 (C.I. 26100), D & C Red No. 33 (C.I. 17200), D & C Orange No. 5 (C.I. 45370), FD & C Yellow No. 5 (C.I. 19140), FD & C Yellow No. 6 (C.I. 15985), D & C Yellow No. 10 (C.I. 47005), D & C Yellow No. 11 (C.I. 47000), D & C Green No. 6 (C.I. 61565), FD & C Blue No. 1 (C.I. 42090), D & C Violet No. 2 (C.I. 60725), ED & C Violet No. 2 (C.I. 60730), and FD & C Red No. 40 (C.I. 16035).

Typical example of natural coloring matter is carmine.

The above-mentioned inorganic pigments, organic pigments, dyestuffs, and natural coloring matters may be used alone or in any mixture thereof.

The typical coloring composition according to the present invention comprises (i) 25% to 99.9% by weight of, preferably 50% to 75% by weight, of gypsum dihydrate and (ii) 0.1% to 75% by weight, preferably 25% to 50% by weight, of at least one coloring agent selected from the group consisting of inorganic pigments, organic pigments, dyestuffs, and natural coloring matters, although the coloring composition is by no means limited to these compositions.

When the amount of the gypsum dihydrate is too small, the color tone of the resultant composition is not so clear. Conversely, when the amount of the gypsum dihydrate is too large, the desired color tone cannot be obtained in the resultant composition.

As mentioned above, the present coloring composition can be effectively produced by mixing (i) gypsum having, as water of crystallization, 0 to 0.5 mole, based on one mole of the gypsum, of water, (ii) at least one coloring agent selected from the group consisting inorganic pigments, organic pigments, dyestuffs, and natural coloring matters, and (iii) water or an aqueous solvent; and after solidification of the mixture, powdering the resultant solid mixture, although the production process of the present coloring composition is not limited to this method. The aqueous solvents usable in the present invention are aqueous solutions containing solvents which are miscible with water and which can be volatilized without remaining in the powder stage. Examples of such solvents are acetone, methyl alcohol, ethyl alcohol, isopropyl alcohol, etc.

The typical production method of the present coloring composition will now be explained in detail.

For example, 25 to 99.9% parts by weight of gypsum having 0 to 0.5 mole of water of crystallization based on 1 mole of gypsum is uniformly mixed, while stirring, with 0.1 to 75 parts by weight of one or more of the above-mentioned coloring agents (i.e., inorganic pigments, organic pigments, dyestuffs, and/or natural coloring matters). To the resultant mixture, 2.5 to 150 parts by weight of water or an aqueous solvent solution is added, followed by stirring, to obtain the uniformly dispersed mixture. The resultant mixture is then allowed to stand at room temperature for 3 to 24 hours, followed by drying at a temperature of, for example, 40° C. to 80° C., in a hot air dryer. The dried mixture is then powdered in any conventional manner, and thus, the desired coloring composition is obtained. Although the size of the powder particles may be controlled over a wide range, the preferable size is 0.01 to 10 μm.

The gypsum-containing coloring composition obtained above according to the present invention can exhibit excellent characteristics when the coloring composition is formulated into, for example, make-up cosmetic base materials. That is, the coloring composition can be uniformly formulated into the base material to provide an excellent clear color tone and not-well-dispersed pigments are not observed. Furthermore, the color tone and the actual color tone upon application are substantially identical. As a result, the present coloring composition may be advantageously and effectively formulated into, for example, various cosmetic compositions, coating compositions, synthetic resins, and other various materials to be colored, as a coloring matter.

Furthermore, the powdered coloring composition according to the present invention can be advantageously subjected to a lipophilic or hydrophilic treatment to expand the application or utility range of the composition. The lipophilic treatment may be carried out in any conventional manner, i.e., a surface treatment with, for example, silicone or a lipophilic surfactant or a surface treatment with, for example, a water-soluble resin such as polyvinyl alcohol or a hydrophilic surfactant.

According to the present invention, the make-up cosmetic composition contains 0.01% to 99% by weight, preferably 1% to 60% by weight, based on the total weight of the cosmetic composition, of the above-mentioned coloring composition.

The make-up cosmetic composition according to the present invention may contain, in addition to the above-mentioned coloring composition, any conventional ingredients as a make-up base material. Examples of these conventional ingredients are inorganic powder materials such as talc, kaolin, sericite, muscovite, synthetic mica, phlogopite, lepidolite, biotite, lithia mica, vermiculite, magnesium carbonate, calcium carbonate, diatomaceous earth, magnesium silicate, calcium silicate, aluminum silicate, barium silicate, strontium silicate, metal tungstenates, silica, and hydroxyapatite; organic powder materials such as nylon powder, polyethylene powder, benzoquanamine powder, polytetrafluoroethylene powder, distyrene benzene pinhole polymer powder, and microcrystalline cellulose; inorganic white pigments such as titanium dioxide and zinc oxide; nacreous pigments such as titanium dioxide coated mica, titanium dioxide coated oxychloro bismuth, oxychloro bismuth, titanium dioxide coated talc, fish scale guanines, and colored titanium dioxide coated mica; metallic powder pigments such as aluminum powder and copper powder; various hydrocarbons such as squalane, liquid paraffin, vaselin, microcrystalline wax, ozokerite, ceresine, myristic acid, palmitic acid, stearic acid, oleic acid, isostearic acid, cetyl alcohol, hexadecyl alcohol, oleyl alcohol, cetyl 2-ethylhexanate, 2-ethylhexyl palmitate, 2-octyldodecyl myristate, neopentyl glycol di-2-ethylhexanate, 2-octyldodecyl oleinate, isopropyl myristate, glycerol triisostearate, glycerol tri(coconut oil fatty acid), olive oil, avogado oil, beewax, myristyl myristate, mink oil, and lanolin; oily components such as higher fatty acids, oil and fats, esters, higher alcohols, and waxes; organic solvents such as acetone, toluene, butyl acetate, and ethyl acetate; resins such as alkyd resins and urea resins; plasticizers such as camphor and acetyltributyl citrate; ultraviolet absorbers; antioxidants; preservers; surfactants; humectants; flavors; water; alcohols; and thickeners.

The cosmetic compositions according to the present invention can be in any conventional form, e.g., in the form of powder, cakes, pencils, sticks, ointments, liquid, emulsions, or creams.

Although cosmetic compositions containing gypsum have been proposed in, for example, JP-B-45-36595 and JP-A-59-93014, the gypsum is used in these cosmetic compositions as an excipient for solidifying the powder ingredients. When gypsum, water, and additives such as extender pigments are kneaded together, followed by casting into a container to solidify, the desired effects of the present invention cannot be expected.

According to the present invention, the coloring compositions containing cosmetic coloring agents solidified with gypsum are formulated into the cosmetic compositions. As a result, the dispersibility of the pigments and the clarity of the color tone, which were not satisfactory this invention, can be remarkably improved. Furthermore, cosmetic compositions having an excellent extendability, coatability, finish appearance, and color tone when applied to the skin, can be obtained.

Now, results of an evaluation of the excellent properties of the color compositions according to the present invention will be explained.

Regarding the clarity of the color tone, the present color composition is compared with simple mixtures of extender pigments and coloring agents obtained by simple mixing and powdering. The results are shown in Table 1.

As the characteristic values, the croma C (i.e., a measure of the color clarity) and the color density $\Delta E_W$ (i.e., a measure of the density or deepness of the color) were compared from the following expressions by using Hunter's L, a, and b values.

$$\text{Croma } C = \sqrt{a^2 + b^2}$$

$$\text{Color density } \Delta E_W = \sqrt{(100 - L)^2 + a^2 + b^2}$$

As is clear from the results shown in Table 1, the values C and $\Delta E_W$ of the present color compositions are larger than those of the comparative compositions. Thus, the superiority of the color tone of the present invention is clear.

TABLE 1

| Coloring agent | Coloring agent conc. (wt. %) | Treatment Conditions | C | $\Delta E_W$ |
| --- | --- | --- | --- | --- |
| Iron red oxide | 50 | Present invention | 34.4 | 63.9 |
| | | Mixture with talc* | 30.4 | 60.5 |
| Iron yellow oxide | 50 | Present invention | 47.9 | 48.1 |
| | | Mixture with talc* | 45.8 | 46.1 |
| C.I. 11680 | 25 | Present invention | 81.1 | 85.1 |
| | | Mixture wth gypsum dihydrate | 78.0 | 82.2 |
| C.I. 73360 | 50 | Present invention | 79.3 | 90.7 |
| | | Mixture with mica* | 75.8 | 86.8 |
| C.I. 15850:1 diluted with BaSO$_4$ | 25 | Present invention | 74.2 | 90.0 |
| | | Mixture with talc* | 63.3 | 79.3 |
| C.I. 74160 | 25 | Present invention | 87.1 | 112.0 |
| | | Mixture with mica* | 79.3 | 99.4 |
| Carmine Al lake | 40 | Present invention | 70.2 | 91.0 |
| | | Mixture with gypsum dihydrate* | 67.9 | 85.2 |

*Both components in the form of powders are mixed while stirring, followed by powdering

EXAMPLES

The present invention will now be further illustrated by, but is by no means limited to, the following Examples, wherein all parts and percentages are expressed on a weight basis unless otherwise noted.

EXAMPLE 1

A 50 part amount of iron red oxide and 50 parts of commercially available calcined gypsum (or plaster of Paris) were mixed, while stirring, in a Henschel mixer to obtain a uniformly dispersed mixture. To the mixture, 100 parts of water was added, followed by mixing with stirring. The resultant mixture was taken in a vat, and after standing at room temperature for one night, the mixture was dried at a temperature of 60° C. for 3 hours in a hot air dryer and then powdered in a grinder.

EXAMPLE 2

A 25 part amount of iron red oxide, 25 parts of iron yellow oxide, and 50 parts of commercially available calcined gypsum (pr plaster of Paris) were mixed, while stirring, in a Henschel mixer to obtain a uniformly dispersed mixture. To the mixture, 125 parts of water was added, followed by mixing with stirring. The resultant mixture was taken in a vat, and after standing at room temperature for one night, the mixture was dried at a temperature of 60° C. for 3 hours in a hot air dryer and then powdered in a grinder.

EXAMPLE 3

A 50 part amount of C.I. 73360 and 50 parts of gypsum anhydride were mixed, while stirring, in a Henschel mixer to obtain a uniformly dispersed mixture. To the mixture, 100 parts of water and 25 parts of ethyl alcohol were added, followed by mixing with stirring. The resultant mixture was taken in a vat, and after standing at room temperature for one night, the mixture was dried at a temperature of 60° C. for 3 hours in a hot air dryer and then powdered in a grinder.

EXAMPLE 4

A 25 part amount of C.I. 11680 pigment, 25 parts of nylon powder, and 50 parts of commercially available calcined gypsum (or plaster of Paris) were mixed, while stirring, in a Henschel mixer to obtain a uniformly dispersed mixture. To the mixture, 100 parts of water and 25 parts of ethyl alcohol were added, followed by mixing with stirring. The resultant mixture was taken in a vat, and after standing at room temperature for one night, the mixture was dried at a temperature of 60° C., for 3 hours in a hot air dryer and then powdered in a grinder.

EXAMPLE 5

A 25 part amount of C.I. 74160, 25 parts of mica titanium type nacreous pigment, and 50 parts of commercially available calcined gypsum (or plaster of Paris) were mixed, while stirring, in a Henschel mixer to obtain a uniformly dispersed mixture. To the mixture, 100 parts of water and 25 parts of ethyl alcohol were added, followed by mixing with stirring. The resultant mixture was taken in a vat, and after standing at room temperature for one night, the mixture was dried at a temperature of 60° C. for 3 hours in a hot air dryer and then powdered in a grinder.

EXAMPLE 6

The coloring composition obtained in Example 1 was subjected to a hydropholic treatment according to Example 1 of JP-B-56-43264. A 97.2 parts amount of the hydropholically treated coloring composition of Example 1 was mixed and ground, together with a 0.4 part of zinc hydroxide, for 10 minutes in a vibrating ball mill. Thereafter, 2.3 parts of methyl hydrogen polysiloxane oil having an SiH equivalent of 77 were added and the mixture was further mixed and ground at room temperature for 30 minutes to effect a crosslinking polymerization reaction. The hydrogen gas generated with the progress of the crosslinking polymerization reaction was removed, together with nitrogen gas, from the system and, thereafter, 1.8 parts of myristic acid was added to effect a neutralization reaction for 30 minutes.

The resultant powder was odorless and had a strong hydropholicity.

EXAMPLE 7

In to 100 parts of water, 5 parts of polyvinylalcohol was dissolved upon heating, followed by adding thereto 95 parts of the coloring composition obtained in Example 1. The mixture was uniformly dispersed in a disper for one hour while stirring, and the dispersed mixture was dried for 3 hours in a hot air dryer and then powdered in a grinder.

COMPARATIVE EXAMPLES 1 and 2

The coloring compositions were prepared in the same manner as in Example 1 except that talc was used instead of the commercial available calcined gypsum (or plaster of Paris).

Although the coloring compositions obtained in Examples 1 and 2 and Comparative Examples 1 and were formulated into cosmetic foundations, the products including the present coloring composition are superior to those of the Comparative Examples in that not-well-dispersed pigments were found and there were no substantial differences between the color before application and the color after application.

COMPARATIVE EXAMPLE 3 hours, the mixture was dried at a temperature of 70° C. for 3 hours in a hot air dryer and then powdered in a grinder, to obtain the coloring composition of Comparative Example 4.

COMPARATIVE EXAMPLES 5 and 6

The coloring compositions of Comparative Examples 5 and 6 were prepared in the same manner as in Comparative Example 4 except that mica and barium sulfate were used, respectively, instead of the talc.

TABLE 2

| Example No. | Pigment | Gypsum used or other treating agent | Solvent | Standing time | Drying condition | Pigment content (%) |
| --- | --- | --- | --- | --- | --- | --- |
| 8 | Iron red oxide | CaSO$_4$ | Water | 6 hr | 60° C. - 3 hr | 40 |
| 9 | " | CaSO$_4$.0.5 H$_2$O | " | 6 hr | 60° C. - 3 hr | 40 |
| 10 | " | CaSO$_4$.2 H$_2$O | " | 6 hr | 60° C. - 3 hr | 40 |
| 11 | Iron yellow oxide | CaSO$_4$ | – | 6 hr | 60° C. - 3 hr | 30 |
| 12 | " | CaSO$_4$.0.5 H$_2$O | " | 6 hr | 60° C. - 3 hr | 30 |
| 13 | " | CaSO$_4$.2 H$_2$O | " | 6 hr | 60° C. - 3 hr | 30 |
| 14 | Iron black oxide | CaSO$_4$ | " | 6 hr | 60° C. - 3 hr | 40 |
| 15 | " | CaSO$_4$.0.5 H$_2$O | " | 6 hr | 60° C. - 3 hr | 40 |
| 16 | " | CaSO$_4$.2 H$_2$O | " | 6 hr | 60° C. - 3 hr | 40 |
| 17 | C.I. 73360 | CaSO$_4$.0.5 H$_2$O | 10% Aqueous ethanol | 12 hr | 70° C. - 3 hr | 25 |
| 18 | " | CaSO$_4$.0.5 H$_2$O | 30% Aqueous ethanol | 12 hr | 70° C. - 3 hr | 25 |
| 19 | " | CaSO$_4$.0.5 H$_2$O | 50% Aqueous ethanol | 12 hr | 70° C. - 3 hr | 25 |
| 20 | C.I. 15850:1 | CaSO$_4$.0.5 H$_2$O | 10% Aqueous ethanol | 24 hr | 60° C. - 3 hr | 30 |
| 21 | C.I. 15850 | CaSO$_4$.0.5 H$_2$O | " | 24 hr | 60° C. - 3 hr | 30 |
| 22 | C.I. 19140:1 | CaSO$_4$.0.5 H$_2$O | 10% Aqueous methanol | 24 hr | 50° C. - 5 hr | 40 |
| 23 | C.I. 74160 | CaSO$_4$.0.5 H$_2$O | " | 24 hr | 50° C. - 5 hr | 40 |
| 24 | Carmine Al | CaSO$_4$.0.5 H$_2$O | 20% Aqueous ethanol | 24 hr | 50° C. - 5 hr | 30 |
| 25 | Marine blue | CaSO$_4$.0.5 H$_2$O | Water | 6 hr | 60° C. - 3 hr | 50 |
| 26 | Prussian blue | CaSO$_4$.0.5 H$_2$O | " | 3 hr | 60° C. - 3 hr | 60 |
| Com. Ex. 4 | C.I. 73360 | Talc | 10% Aqueous ethanol | 12 hr | 70° C. - 3 hr | 25 |
| Com. Ex. 5 | " | Mica | " | 12 hr | 70° C. - 3 hr | 25 |
| Com. Ex. 6 | " | BaSO$_4$ | " | 12 hr | 70° C. - 3 hr | 25 |

The coloring composition was prepared in the same manner as in Example 3, except that mica was used instead of gypsum anhydride.

The color tone of the powder solid type eyeshadow containing the present coloring composition formulated therein was clearer than that of Comparative Example 3.

EXAMPLE 8

A 40% amount of iron red oxide and 60% of commercially available calcined gypsum (or plaster of Paris) were mixed, while stirring, in a Henschel mixer to obtain a uniformly dispersed mixture. To the mixture, 100% of water was added, followed by mixing with stirring. The resultant mixture was taken in a vat, and after standing at room temperature for one night, the mixture was dried at a temperature of 60° C. for 3 hours in a hot air dryer and then powdered in a grinder, to obtain the coloring composition of Example 8.

EXAMPLES 9 to 26

Various coloring compositions were prepared in the same manner as in Example 8, except that the iron red oxide, the calcined gypsum, the standing time, and the drying condition were changed as shown in Table 2.

COMPARATIVE EXAMPLE 4

A 25% amount of C.I. 73360 and 75% amount of talc were mixed, while stirring, in a Henschel mixer to obtain a uniformly dispersed mixture. To the mixture, 90% of water and 10% ethanol were added, followed by mixing with stirring. The resultant mixture was taken in a vat, and after standing at room temperature for 12

Various cosmetic make-up compositions were prepared by formulating the coloring compositions obtained above.

The clarity of the resultant cosmetic compositions were evaluated by using Hunter's L, a, and b values as follows:

$$\text{Croma } C = \sqrt{a^2 + b^2}$$

$$\text{Color density } \Delta E_W = \sqrt{(100 - L)^2 + a^2 + b^2}$$

The larger the values C and $\Delta E_W$, the greater the clarity.

The organoleptic evaluation of the resultant cosmetic compositions was carried out by using an expert panel of 20 members for each item, based upon five stage evaluation points (see Table 3). The results are shown on average based upon the following criteria.

⊙ . . . 4.5 to 5.0
○ . . . 3.5 to less than 4.5
△ . . . 2.5 to less than 3.5
x . . . 1.5 to less than 2.5
xx . . . 1.0 to less than 1.5

TABLE 3

| Point | Adhesion Spreadability, Finished Color Appearance Tackiness, Sensation of Cooleness Transparency | Change of Skin Condition After 2 Hrs. | Shading | Finished Look |
| --- | --- | --- | --- | --- |
| 1 | Very poor | Very poor | Very difficult | Very poor |
| 2 | Poor | Poor | Difficult | Poor |
| 3 | Normal | Normal | Normal | Normal |
| 4 | Fair | Good | Easy | Good |
| 5 | Good | Excellent | Very easy | Excellent |

EXAMPLE 27 POWDER FOUNDATION

A powdery foundation A according to the present invention was prepared from the following ingredients.

| Ingredient | % |
| --- | --- |
| (1) Titanium dioxide | 7 |
| (2) Talc | 40 |
| (3) Mica | 26.4 |
| (4) Nylon powder | 12 |
| (5) Coloring composition of Example 8 (Iron red oxide) | 1 |
| (6) Coloring composition of Example 11 (Iron yellow oxide) | 2 |
| (7) Coloring composition of Example 14 (Iron black oxide) | 0.2 |
| (8) Silicone oil | 1 |
| (9) 2-Ethylhexyl palmitate | 9 |
| (10) Sorbitan sesquioleate | 1 |
| (11) Preservative | 0.3 |
| (12) Flavor | 0.1 |

The ingredients (1) to (7) were mixed in a Henschel mixer, and thereafter a mixture of the ingredients (8) to (12) previously dissolved and mixed upon heating was added thereto, and the mixture was powdered in a 5 HP pulverizer (manufactured by Hosokawa Micron K.K., the same hereinbelow). The powder was molded in an inside dish to obtain the desired powdery foundation A.

The powdery foundations B and C were prepared in the same manner as mentioned above, except that the coloring compositions obtained in Examples 9, 12, and 15 and in Examples 10, 13, and 16, respectively, were used instead of those of Examples 8, 11, and 14.

Furthermore, a comparative powdery foundation X was prepared in the same manner as mentioned above, except that 0.4% of iron red oxide, 0.6% of iron yellow oxide, 0.08% of iron black oxide, and 2.12% of mica were used instead of the coloring compositions of Examples 8, 11, and 14.

The evaluation results are shown in Table 4.

TABLE 4

| Powdery foundation | Spreadability | Adhesion | Finished Look | C | $\Delta E_W$ |
| --- | --- | --- | --- | --- | --- |
| A*1 | ○ | ○ | ⊚ | 8.7 | 22.1 |
| B*1 | ⊚ | ⊚ | ⊚ | 8.9 | 22.0 |
| C*1 | ○ | ○ | ⊚ | 8.2 | 21.8 |
| X*2 | △ | △ | △ | 5.5 | 18.2 |

*1 Present invention
*2 Comparative

As is clear from the results shown in Table 4, the powdery foundations according to the present invention obtained good results in all the evaluation items irrespective of the type of gypsum used.

EXAMPLE 28 BRUSHER

The brusher A according to the present invention was prepared from the following ingredients.

| Ingredient | % |
| --- | --- |
| (1) Talc | 33.5 |
| (2) Mica | 51 |
| (3) Titanium dioxide | 3 |
| (4) Coloring composition of Example 17 (C.I. 73360) | 4 |
| (5) Squalane | 3 |
| (6) 2-Ethylhexyl palmitate | 5 |
| (7) Preservative | 0.3 |
| (8) Flavor | 0.2 |

The ingredients (1) to (4) were mixed in a Henschel mixer and a mixture of the ingredients (5) to (8) previously dissolved and mixed upon heating was then sprayed onto the resultant mixture. After the mixture was further mixed, the mixture was powdered in the 5 HP pulverized and the powdered mixture was molded in an inside dish to obtain the desired brusher A.

On the other hand, a comparative brushers X, Y, Z and W was prepared in the same manner as mentioned above, except that coloring agents prepared in Comparative Examples 4, 5, and 6, and 3% of mica and 1% of C.I. 73360 were used instead of the coloring composition of the above ingredients (4).

The evaluation results are shown in Table 5.

TABLE 5

| Brusher | Spreadability | Adhesion | Shading | Transparency | Finished Look | C | $\Delta E_W$ |
| --- | --- | --- | --- | --- | --- | --- | --- |
| A*1 | ⊚ | ⊚ | ⊚ | ⊚ | ⊚ | 13.9 | 26.2 |
| X*2 | ○ | ○ | ○ | △ | ○ | 12.0 | 24.9 |
| Y*2 | ○ | ○ | ○ | △ | △ | 11.8 | 24.9 |
| Z*2 | △ | ○ | ○ | △ | △ | 11.8 | 25.5 |
| W*2 | △ | △~○ | △ | x | x | 9.5 | 21.3 |

*1 Present invention
*2 Comparative

As is clear from the results shown in Table 5, the brusher A according to the present invention showed excellent results in all the evaluation items.

EXAMPLE 29 EYESHADOW

The eyeshadow A according to the present invention was prepared from the following ingredients:

| Ingredient | % |
| --- | --- |
| (1) Talc | 48.4 |
| (2) Mica | 33 |
| (3) Coloring composition of Example 25 (Ultramarine blue) | 8 |

-continued

| Ingredient | % |
|---|---|
| (4) Coloring composition of Example 9 (Iron red oxide) | 4 |
| (5) Coloring composition of Example 15 (Iron black oxide) | 1.5 |
| (6) Liquid paraffin | 4 |
| (7) Sorbitan sesquioleate | 0.8 |
| (8) Preservative | 0.1 |
| (9) Flavor | 0.2 |

The ingredients (1) to (5) were mixed in a Henschel mixer and a mixture of the ingredients (6) to (9) previously mixed and dissolved upon heating was sprayed onto the resultant mixture. After the mixture was further mixed, the mixture was powdered in the 5 HP pulverizer and was molded in an inside dish to obtain the desired eyeshadow A.

A comparative eyeshadow X was prepared in the same manner as mentioned above except that 4% of ultramarine blue, 1.2% of iron red oxide, 0.6% of iron black oxide, and 7.7% of mica was used instead of the coloring compositions (3), (4), and (5).

The evaluation results are shown in Table 6.

TABLE 6

| Eye shadow | Spreadability | Adhesion | Shading | Finished Look | C | $\Delta E_W$ |
|---|---|---|---|---|---|---|
| A*1 | ⊚ | o | ⊚ | ⊚ | 35.6 | 45.9 |
| X*2 | Δ | Δ | Δ | x | 30.3 | 43.0 |

*1 Present invention
*2 Comparative

As is clear from the results shown in Table 6, the eyeshadow according to the present invention was superior, in all the evaluation items, to the comparative eyeshadow X.

EXAMPLE 30 OILY STICK FOUNDATION

The oily stick foundation A according to the present invention was prepared from the following ingredients:

| Ingredient | % |
|---|---|
| (1) Titanium dioxide | 13 |
| (2) Kaolin | 12 |
| (3) Talc | 9.5 |
| (4) Coloring composition of Example 9 (Iron red oxide) | 3 |
| (5) Coloring composition of Example 12 (Iron yellow oxide) | 2 |
| (6) Coloring composition of Example 15 (Iron black oxide) | 1 |
| (7) Squalane | 37 |
| (8) Cetyl 2-ethylhexanate | 16 |
| (9) Sorbitan sesquioleate | 1 |
| (10) Solid paraffine | 4 |
| (11) Carnauba wax | 1.3 |
| (12) Flavor | 0.2 |

The component (7) to (9) were mixed at 80° C., followed by adding the ingredients (1) to (6). After the resultant mixture was mixed in a disper, the dispersed mixture was treated in a TK mill. Thereafter, the ingredients (10) and (11) were dissolved upon heating, followed by adding to the above mixture. The mixture was then degassed and the ingredient (12) was gradually mixed therewith. The resultant mixture was packed into a container at 80° C., followed by cooling to obtain the desired stick foundation A.

A comparative stick foundation X was prepared in the same manner as mentioned above, except that 1.2% of iron red oxide, 0.6% of iron yellow oxide, 0.4% of iron black oxide, and 3.8% of talc were used instead of the coloring compositions (4), (5), and (6).

The evaluation results are shown in Table 7.

TABLE 7

| Stick foundation | Spreadability | Adhesion | Sensation of Coolness | Finished Look | C | $\Delta E_W$ |
|---|---|---|---|---|---|---|
| A*1 | ⊚ | ⊚ | ⊚ | ⊚ | 20.8 | 30.1 |
| X*2 | Δ | o | o | Δ | 18.0 | 26.5 |

*1 Present invention
*2 Comparative

As is clear from the results shown in Table 7, the stick foundation according to the present invention obtained excellent results in all the evaluation items.

EXAMPLE 31 EMULSIFIED FOUNDATION

The emulsified foundation according to the present invention was prepared from the following ingredients:

| Ingredient | % |
|---|---|
| (1) Stearic acid | 0.4 |
| (2) Isostearic acid | 0.3 |
| (3) Cetyl 2-ethylhexanate | 4 |
| (4) Liquid paraffin | 11 |
| (5) Polyoxyethylene (10 mole) Stearyl ether | 2 |
| (6) Talc | 15 |
| (7) Coloring composition of Example 9 (Iron red oxide) | 4 |
| (8) Coloring composition of Example 12 (Iron yellow oxide) | 2 |
| (9) Coloring composition of Example 15 (Iron black oxide) | 1 |
| (10) Cetyl alcohol | 0.3 |
| (11) Preservative | 0.07 |
| (12) Triethanol amine | 0.42 |
| (13) Propylene glycol | 5 |
| (14) Preservative | 0.2 |
| (15) Ion exchanged water | 54.19 |
| (16) Flavor | 0.3 |

After the ingredients (1) to (12) were dissolved and mixed upon heating at 85° C., a mixture of the ingredients (13) to (16) previously dissolved and mixed upon heating was gradually added and emulsified. The temperature during emulsifying was maintained for 10 minutes while stirring and was then cooled to 45° C. while stirring. The ingredient (17) was then added to the resultant emulsified mixture, followed by cooling to 35° C. while stirring. The product was recovered and filled into a container to prepare the desired emulsified foundation A.

A comparative emulsified foundation X was prepared in the same manner as mentioned above except that 1.6% of iron red oxide, 0.6% of iron yellow oxide, 0.4% of iron black oxide, and 4.4% of talc were used instead of the coloring compositions (8) to (10).

The evaluation results are shown in Table 8.

TABLE 8

| Emulsified foundation | Spreadability | Adhesion | Transparency | Finished Look | C | $\Delta E_W$ |
|---|---|---|---|---|---|---|
| A*1 | o | ⊚ | o | ⊚ | 15.8 | 28.3 |

TABLE 8-continued

| Emulsified foundation | Spread-ability | Ad-hesion | Trans-parency | Finished Look | C | ΔE$_H$ |
|---|---|---|---|---|---|---|
| X*² | Δ | Δ | Δ | Δ | 12.9 | 26.2 |

*¹Present invention
*²Comparative

As is clear from the results shown in Table 8, the emulsified foundation A according to the present invention obtained excellent results in all the evaluation items, when compared to the comparative foundation X. Furthermore, the present foundation A showed an excellent stability with the elapse of time (i.e., no decomposition occurred).

EXAMPLE 32 OILY LIPSTICK

The oily lipstick A according to the present invention was prepared from the following ingredients:

| Ingredient | % |
|---|---|
| (1) Hydrocarbon wax | 3 |
| (2) Candelilla wax | 1 |
| (3) Glycerol triisostearate | 40 |
| (4) Liquid paraffin | 45.8 |
| (5) Titanium dioxide | 4 |
| (6) Coloring composition of Example 20 (C.I. 15850:1) | 3 |
| (7) Coloring composition of Example 21 (C.I. 15850) | 3 |
| (8) Flavor | 0.2 |

The ingredients (1) to (4) were dissolved upon heating at 85° C. and, after mixing the resultant mixture with the ingredients (5) to (7), the ingredient (8) was mixed, while stirring. The resultant mixture was filled into a container to obtain the desired oily lipstick A.

A comparative oily lipstick X was prepared in the same manner as mentioned above, except that 0.9% of C.I. 15850:1, 0.9% of C.I. 15850, and 1.2% of mica were used instead of the coloring compositions (6) and (7).

The evaluation results are shown in Table 9.

TABLE 9

| Oily lipstick | Spread-ability | Adhesion | Change of Skin Condition After 2 Hrs | Finished Look | C | ΔE$_W$ |
|---|---|---|---|---|---|---|
| A*¹ | o | o | ⊙ | o | 75.6 | 88.7 |
| X*² | Δ | Δ | Δ | Δ | 72.0 | 84.3 |

*¹Present invention
*²Comparative

As is clear from the results shown in Table 9, the oily lipstick according to the present invention was superior, in all the evaluation items, to the comparative oily lipstick X.

EXAMPLE 33 EMULSIFIED LIPSTICK

The emulsified lipstick A according to the present invention was prepared from the following ingredients:

| Ingredient | % |
|---|---|
| (1) Polyethylene | 7 |
| (2) Ceresin | 4 |
| (3) Candelilla wax | 7 |
| (4) Carnauba wax | 1 |
| (5) Castor oil | 20 |
| (6) Liquid paraffin | 23.3 |
| (7) Glycerol tristearate | 20 |
| (8) Titanium coated mica | 5 |
| (9) Coloring composition of Example 22 (C.I. 19140:1) | 1 |
| (10) Coloring composition of Example 24 (Carmine Al lake) | 0.3 |
| (11) Coloring composition of Example 21 (C.I. 15850) | 0.2 |
| (12) Dibutyl hydroxytoluene | 0.1 |
| (13) Flavor | 0.1 |
| (14) Sorbitan sesquioleate | 2 |
| (15) Purified water | 5 |
| (16) Propylene glycol | 2 |
| (17) Sorbitol | 2 |

The ingredients (1) to (7) were dissolved upon heating at 90° C. in a pot, followed by adding the ingredients (8) to (13) to be dispersed. Furthermore, the ingredients (14) and (17) were gradually added and mixed while stirring. Thereafter, the ingredients (15) and (16) were gradually added at 80° C., followed by mixing while stirring. The resultant mixture was filled into a container and was molded to obtain the desired emulsified lipstick A.

A comparative emulsified lipstick X was prepared in the same manner as mentioned above except that 0.4% of C.I. 19140:1, 0.09% of Carmine Al lake, 0.06% of Red #201, and 0.41% of mica were used instead of the coloring compositions (9) to (11).

The evaluation results are shown in Table 10.

TABLE 10

| Emul-sified lipstick | Spread-ability | Adhesion | Change of Skin Condition After 2 Hrs | Finished Look | C | ΔE$_W$ |
|---|---|---|---|---|---|---|
| A*¹ | o | o | ⊙ | o | 41.3 | 43.5 |
| X*² | Δ | Δ | Δ | Δ | 37.5 | 40.1 |

*¹Present invention
*²Comparative

As is clear from the results shown in Table 10, the emulsified lipstick A according to the present invention was superior, in all the evaluation items, to the comparative lipstick X.

EXAMPLE 34 PENCIL TYPE EYELINER

The pencil type eyeliner A according to the present invention was prepared from the following ingredients:

| Ingredient | % |
|---|---|
| (1) Hydrogenated castor oil | 15 |
| (2) Hydrocarbon wax | 6 |
| (3) Candelilla wax | 5 |
| (4) Stearic acid | 12 |
| (5) Isopropyl myristate | 10.95 |
| (6) Sorbitan sesquioleate | 1 |
| (7) Antioxidant | 0.05 |
| (8) Titanium dioxide | 5 |
| (9) Coloring composition of Example 15 Iron black oxide) | 45 |

The ingredients (1) to (7) were dissolved at 85° C. upon heating and, after the ingredients (8) and (9) were added thereto, the mixture was stirred. The resultant mixture was injection molded using an injection molding machine for a pencil, followed by setting in a wood surround to obtain the desired pencil type eyeliner A.

A comparative pencil type eyeliner X was prepared in the same manner as mentioned above except that 18% of iron black oxide and 27% of mica were used instead of the coloring composition (9).

The results are shown in Table 11.

TABLE 11

| Pencil type eyeliner | Spread-ability | Adhesion | Finished Color Appearance | Finished Look | $\Delta E_W$ |
|---|---|---|---|---|---|
| A*1 | o | o | ⊚ | ⊚ | 89.3 |
| X*2 | x | Δ | Δ | Δ | 83.0 |

*1 Present invention
*2 Comparative

As is clear from the results shown in Table 11, the pencil type eyeliner A according to the present invention was superior, in all the evaluation items, to the comparative pencil type eyeliner X.

EXAMPLE 35 EYELINER

The eyeliner A according to the present invention was prepared from the following ingredients:

| Ingredient | % |
|---|---|
| (1) Coloring composition of Example 15 (Iron black oxide) | 7 |
| (2) Coloring composition of Example 9 (Iron red oxide) | 5 |
| (3) Titanium dioxide | 2 |
| (4) Vinylacetate resin emulsion | 45 |
| (5) Glycerol | 6 |
| (6) Polyoxyethylene (20) sorbitan monolaurate | 1.8 |
| (7) Carboxy methylcellulose (10% aqueous solution) | 18 |
| (8) Montomorilonite (5% aqueous dispersion) | 5 |
| (9) Ion exchanged water | 9.9 |
| (10) Preservative | 0.1 |
| (11) Flavor | 0.2 |

The ingredients (5) and (6) were added to the ingredient (9), followed by adding the ingredients (1) to (3). The resultant mixture (i.e., pigment part) was subjected to a colloid mill treatment. The other ingredients were mixed, and the above-prepared pigment part was added at 70° C. to the resultant mixture, followed by a uniform dispersion. After cooling, the dispersed mixture was filled into a container to obtain the desired eyeliner A.

A comparative eyeliner X was prepared in the same manner as mentioned above, except that 2.8% of iron black oxide, 2% of iron red oxide, and 7.2% of talc were used instead of the coloring compositions (1) and (2).

The evaluation results are shown in Table 12.

TABLE 12

| Eyeliner | Spread-ability | Adhesion | Finished Color Appearance | Finished Look | $\Delta E_W$ |
|---|---|---|---|---|---|
| A*1 | ⊚ | o | ⊚ | ⊚ | 69.9 |
| X*2 | Δ | Δ | Δ | Δ | 65.5 |

*1 Present invention
*2 Comparative

As is clear from the results shown in Table 12, the eyeliner A according to the present invention was superior, in all the evaluation items, to the comparative eyeliner X.

EXAMPLE 36 MASCARA

The mascara A according to the present invention was prepared from the following ingredients:

| Ingredient | % |
|---|---|
| (1) Carnauba wax | 20 |
| (2) Cetanol | 5 |
| (3) Liquid paraffin | 52.4 |
| (4) Sorbitan sesquioleate | 2.5 |
| (5) Dimethyl dialkyl ammonium hectorite | 3 |
| (6) Aluminum stearate | 5 |
| (7) Paraoxybenzoic acid ester | 0.05 |
| (8) Coloring composition of Example 15 (Iron red oxide) | 12 |

The ingredients (1) and (2) were melted. The ingredients (4) to (8) were dispersed and dissolved in the ingredient (3), followed by the above molten ingredients (1) and (2). After the resultant mixture was uniformly mixed while stirring, the mixture was cooled to 50° C. and was filled into a container, to obtain the desired mascara A.

A comparative mascara X was prepared in the same manner as mentioned above, except that 4.8% of iron black oxide and 7.2% of talc were used instead of the comparative mascara X.

The evaluation results are shown in Table 13.

TABLE 13

| Mascara | Spread-bility | Adhesion | Sensation of Color | Finished Look | Finished Color Appearance | $\Delta E_W$ |
|---|---|---|---|---|---|---|
| A*1 | ⊚ | o | o | ⊚ | ⊚ | 77.1 |
| X*2 | Δ | Δ | Δ | Δ | Δ | 74.3 |

*1 Present invention
*2 Comparative

As is clear from the results shown in Table 13, the mascara A according to the present invention was superior, in all the evaluation items, to the comparative mascara X.

EXAMPLE 37 NAIL ENAMEL

The nail enamel A according to the present invention was prepared from the following ingredients:

| Ingredient | % |
|---|---|
| (1) Nitrocellulose | 12 |
| (2) Modified alkyd resin | 12 |
| (3) Acetyltributyl citrate | 5 |
| (4) n-Butyl acetate | 36.4 |
| (5) Ethyl acetate | 6 |
| (6) n-Butyl alcohol | 2 |
| (7) Toluene | 21 |
| (8) Coloring composition of Example 23 (C.I. 74160) | 2.6 |
| (9) Titanium mica | 2 |
| (10) Organically modified montmorilonite | 1 |

The ingredients (1) to (7) (provided that a part of the ingredient (4) was used) were dissolved and, to the resultant solution, a gelled mixture of the component (4) and the remainder of the component (4) were added and mixed together, followed by adding the components (8) to (10). The resultant mixture was filled into a container to obtain the desired nail enamel A.

A comparative nail enamel X was prepared in the same manner as mentioned above, except that 1.04% of C.I. 74160 and 1.56% of mica were used instead of the coloring composition (8).

The evaluation results are shown in Table 14.

TABLE 14

| Nail enamel | Spread-ability | Adhesion | Finished Color Appearance | Finished Look | Tackiness | C | ΔE$_W$ |
|---|---|---|---|---|---|---|---|
| A*1 | ⊚ | ○ | ⊚ | ⊚ | ⊚ | 82.3 | 77.1 |
| X*2 | △ | △ | △ | △ | △ | 75.1 | 74.3 |

*1 Present invention
*2 Comparative

As is clear from the results shown in Table 14, the nail enamel A according to the present invention was superior, in all the evaluation items, to the comparative nail enamel X.

EXAMPLE 38 NIGHT CREAM (WATER-IN-OIL TYPE)

The W/O type night cream A according to the present invention was prepared from the following ingredients:

| Ingredient | % |
|---|---|
| (1) Squalane | 14.99 |
| (2) Olive oil | 15 |
| (3) Beeswax | 2 |
| (4) Hydrogenated lanolin alcohol | 3 |
| (5) Ceresin | 2 |
| (6) Polyoxyethylene (10) polyoxypropylene (20) 2-decyl-tetradecyl ether | 3 |
| (7) Butyl benzoate | 0.1 |
| (8) Flavor | 0.1 |
| (9) Coloring composition of Example 21 (C.I. 15850) | 0.01 |
| (10) Water | 54.5 |
| (11) Sodium chondroitin sulfate | 0.3 |
| (12) Propylene glycol | 5 |

After the ingredients (1) to (8) were dissolved at 75° C., the ingredient (9) was added thereto, followed by mixing while stirring. The ingredients (10) to (12) were separately dissolved at 75° C. and the solution was added to the above-prepared mixture, while stirring. Then, after emulsifying in a homomixer, the mixture was cooled to room temperature while stirring and the cooled product was filled into a container to obtain the desired W/O type night cream A.

A comparative W/O type night cream X was prepared in the same manner as mentioned above, except that 0.003% Red #201 and 0.007% of mica were used instead of the coloring composition (10).

The results of the organoleptical evaluation of the night creams A and X showed that the W/O type night cream according to the present invention had no not-well-dispersed pigments caused by non-uniform dispersion, had a clear color tone and exhibited an improved, for example, extendability and refreshing effect.

We claim:

1. A coloring composition comprising (i) 25% to 99.9% by weight of gypsum dihydrate and (ii) 0.1% to 75% by weight of at least one coloring agent.

2. A coloring composition according to claim 1, wherein the coloring agent comprises carmine.

3. A cosmetic composition containing (A) a cosmetic base composition and (B) a coloring composition according to claim 1, wherein the content of the coloring composition is 0.01% to 99.% by weight in the cosmetic composition.

4. A method for producing a coloring composition comprising the steps of:
   mixing (i) 25 to 99.9 parts by weight of gypsum having, as water of crystallization, 0 to 0.5 mole, based on one mole of the gypsum, of water, (ii) 0.1 to 75 parts by weight of at least one coloring agent and (iii) 25 to 150 parts by weight, based upon 100 parts by weight of the total amount of the components (i) and (ii), of water or an aqueous solvent solution;
   drying the resultant mixture at a temperature of 40° C. to 80° C.; and
   after solidification powdering the resultant solid mixture.

5. The method according to claim 4, wherein the coloring agent comprises carmine.

6. A coloring composition produced by the process of claim 4.

* * * * *

UNITED STATES PATENT AND TRADEMARK OFFICE
CERTIFICATE OF CORRECTION

PATENT NO. : 5,221,342

DATED : June 22, 1993

INVENTOR(S) : Minami, et al.

It is certified that error appears in the above-identified patent and that said Letters Patent is hereby corrected as shown below:

Col. 18, line 42   Delete " after solidification "

Signed and Sealed this

Twenty-second Day of November, 1994

Attest:

BRUCE LEHMAN

*Attesting Officer*          *Commissioner of Patents and Trademarks*